(12) United States Patent
Liebenberg et al.

(10) Patent No.: US 8,901,089 B2
(45) Date of Patent: Dec. 2, 2014

(54) COMPOSITION COMPRISING AN AMORPHOUS NON-CRYSTALLINE GLASS FORM OF ROXITHROMYCIN

(75) Inventors: Wilna Liebenberg, Potchefstroom (ZA); Marique Aucamp, Potchefstroom (ZA); Melgardt M De Villiers, Madison, WI (US)

(73) Assignee: North-West University (ZA)

( * ) Notice: Subject to any disclaimer, the term of this patent is extended or adjusted under 35 U.S.C. 154(b) by 95 days.

(21) Appl. No.: 13/516,864

(22) PCT Filed: Dec. 15, 2010

(86) PCT No.: PCT/IB2010/055841
§ 371 (c)(1),
(2), (4) Date: Nov. 2, 2012

(87) PCT Pub. No.: WO2011/073926
PCT Pub. Date: Jun. 23, 2011

(65) Prior Publication Data
US 2013/0045936 A1 Feb. 21, 2013

(30) Foreign Application Priority Data
Dec. 18, 2009 (ZA) .................................. 2009/09098

(51) Int. Cl.
*A61K 31/70* (2006.01)
*C07H 17/08* (2006.01)
*C07H 1/00* (2006.01)

(52) U.S. Cl.
CPC . *C07H 17/08* (2013.01); *C07H 1/00* (2013.01)

USPC .............................. 514/29; 536/7.2; 536/7.4

(58) Field of Classification Search
CPC ......................................................... C07H 17/08
USPC .............................................. 536/7.2, 29, 7.4
See application file for complete search history.

(56) References Cited

PUBLICATIONS

"International Application Serial No. PCT/IB2010/055841, International Search Report mailed Apr. 6, 2011", 2 pgs.
Biradar, S. V., et al., "A comparative study of approaches used to improve solubility of roxithromycin", Powder Technology, 169(1), (2006), 22-32.

*Primary Examiner* — Elli Peselev
(74) *Attorney, Agent, or Firm* — Schwegman Lundberg & Woessner, P.A.

(57) ABSTRACT

The invention relates to an amorphous non-crystalline glass form (Form-II) of 3R,4S,5S,6R,7R,9R,11S,12R,13S,14R-6-[(2S,3R,4S,6R)-4-dimethylamino-3-hydroxy-6-methyloxan-2-yl]oxy-14-ethyl-7,12,13-trihydroxy-4-[(2R,4R,5S,6S)-5-hydroxy-4-methoxy-4,6-dimethyloxan-2-yl]oxy-10-(2-methoxyethoxymethoxyimino)-3,5,7,9,11,13-hexamethyl-1-oxa-cyclotetradecan-2-one or roxithromycin having at least one characteristic infra-red spectrum peak at approximately 3580 to 3464 cm$^{-1}$. The invention further relates to a preparation method of increasing the solubility of roxithromycin including the steps of selecting anhydrous roxithromycin or monohydrated roxithromycin; elevating the temperature of the roxithromycin to above the melting point thereof; and reducing the temperature of the melt sufficiently to allow it to set into an amorphous non-crystalline glass form (Form-II) of roxithromycin having relatively increased solubility without decreasing the stability of thereof.

12 Claims, 6 Drawing Sheets

COMPOSITION COMPRISING AN AMORPHOUS NON-CRYSTALLINE GLASS FORM OF ROXITHROMYCIN

RELATED APPLICATION

This application is a nationalization under 35 U.S.C. 371 of PCT/IB2010/055841, filed Dec. 15, 2010 and published as WO 2011/0732926 A1 on Jun. 23, 2011, which claimed priority to South African Patent Application Ser. No. 2009/09098, filed Dec. 18, 2009; which applications and publication are incorporated herein by reference and made a part hereof.

INTRODUCTION AND BACKGROUND TO THE INVENTION

This invention relates to a macrolide composition. More particularly this invention relates to a novel polymorph form, (Form-II), of 3R,4S,5S,6R,7R,9R,11S,12R,13S,14R-6-[(2S,3R,4S,6R)-4-dimethylamino-3-hydroxy-6-methyloxan-2-yl]oxy-14-ethyl-7,12,13-trihydroxy-4-[(2R,4R,5S,6S)-5-hydroxy-4-methoxy-4,6-dimethyloxan-2-yl]oxy-10-(2-methoxyethoxymethoxyimino)-3,5,7,9,11,13-hexamethyl-1-oxacyclotetradecan-2-one or roxithromycin. This invention further relates to a preparation method of a medicament. More particularly this invention relates to a method of increasing the solubility of roxithromycin.

Roxithromycin, a 14-membered-ring, macrolide antibiotic, is very similar in composition, chemical structure (semi-synthetic) and mechanism of action to erythromycin. Roxithromycin is currently available in two forms, namely anhydrous and monohydrate form.

Roxithromycin exhibits activity against some sexually transmitted diseases, upper and lower respiratory tract infections, asthma, gum infections like gingivitis, and bacterial infections associated with stomach and intestinal ulcers. Roxithromycin is regarded as the drug of choice for the treatment of opportunistic infections occurring in HIV/AIDS patients, owing to its activity against *Cryptosporidium* spp., *Mycobacterium avium* complex, *Pneumocystis carinii* and *Toxoplasma gondii*.

A disadvantage associated with roxithromycin is that it is a hydrophobic molecule, with no free hydroxyl groups and it is thus poorly water-soluble and unstable in an acidic environment.

A further disadvantage associated with roxithromycin is that its poor water-solubility and instability in an acidic environment results in a decrease in the absorption and bioavailability thereof.

Yet another disadvantage of roxithromycin is that said decreased absorption and bioavailability require relatively large quantities of roxithromycin to be administered in order to achieve a therapeutic effect.

A disadvantage associated with the use of relative large quantities of roxithromycin is that there is a potential increase in the side-effects associated with this active ingredient.

An even further disadvantage associated with the use of relative large quantities of roxithromycin is that there is an increase in the production and manufacturing cost of the product, thereby increasing the cost of treatment.

OBJECTS OF THE INVENTION

An object of the present invention is to provide a novel form of roxithromycin. Another object of the invention is to provide a method for increasing the solubility of roxithromycin. Yet another object of the invention is to provide a medicament prepared in accordance with such a method with which the aforesaid disadvantages may be overcome or at least minimised.

SUMMARY OF THE INVENTION

According to a first aspect of the invention there is provided a composition comprising an amorphous non-crystalline glass form (Form-II) of roxithromycin.

The amorphous non-crystalline glass form (Form-II) of roxithromycin may display an infra-red spectrum having at least one characteristic peak at approximately 3580 to 3464 $cm^{-1}$. The infra-red spectrum may be substantially depicted as in FIG. 8.

The amorphous non-crystalline glass form (Form-II) of roxithromycin may exhibit a powder X-ray diffraction pattern substantially as depicted in FIG. 9.

The amorphous non-crystalline glass form (Form-II) of roxithromycin may display a differential scanning calorimetry thermogram substantially as depicted in FIG. 2 and exhibit a glass transition between 75 and 78 degrees Celsius.

The amorphous non-crystalline glass form (Form-II) of roxithromycin may have a 20%, preferably a 75%, increased solubility relative to anhydrous roxithromycin or monohydrated roxithromycin between pH 4.5 to pH 7.

According to a second aspect of the invention there is provided a method of increasing the solubility of roxithromycin including the steps of:
  providing roxithromycin selected from the group consisting of anhydrous roxithromycin or monohydrated roxithromycin;
  elevating the temperature of the roxithromycin to above the melting point thereof; and reducing the temperature of the melt sufficiently to allow it to set into an amorphous non-crystalline glass form (Form-II) of roxithromycin having relatively increased solubility without decreasing the stability thereof.

The step of elevating the temperature of the roxithromycin to above its melting point includes the step of elevating the temperature thereof to between 100 and 140 degrees Celsius, preferably 120 degrees Celsius so as to not cause degradation thereof.

According to a third aspect of the invention there is provided a medicament prepared from anhydrous roxithromycin or monohydrated roxithromycin in accordance with the method of the second aspect of the invention.

According to a fourth aspect of the invention there is provided use of a pharmaceutically effective amount of an amorphous non-crystalline glass form (Form-II) of roxithromycin in accordance with the first aspect of the invention and prepared in accordance with the method of the second aspect of the invention in a method of treating a patient suffering from opportunistic illnesses associated with immune deficiency conditions.

According to a fifth aspect of the invention there is provided use of a pharmaceutically effective amount of an amorphous non-crystalline glass form (Form-II) in accordance with the first aspect of the invention and prepared in accordance with the method of the second aspect of the invention in a method of preparing a medicament for use in treating a patient suffering from opportunistic disease associated with immune deficiency conditions.

According to a sixth aspect of the invention there is provided a method of treating a patient suffering from opportunistic diseases associated with immune deficiency conditions including the step of administering to such a patient a pharmaceutically effective amount of an amorphous non-crystalline glass form (Form-II) of roxithromycin in accordance with the first aspect of the invention and prepared in accordance with the method of the second aspect of the invention.

According to yet another aspect of the invention there is provided a medicament prepared from an amorphous non-crystalline glass form (Form-II) of roxithromycin in accordance with the method of the second aspect of the invention, together with at least one inert pharmaceutically acceptable carrier or diluents in the dosage form selected from the group consisting of enteric coated tablets; capsules; solutions; syrups; suspensions; bolus injection; continuous infusion; powder for reconstitution; ointments; creams; gels; lotions; sprays, enemas, douche, pessary, transdermal patch, dermal patch and lozenges.

BRIEF DESCRIPTION OF THE DRAWINGS

The invention will now be described further, by way of example only, with reference to the accompanying drawings wherein.

DESCRIPTION OF A PREFERRED EMBODIMENT OF THE INVENTION

According to a preferred embodiment of the invention there is provided a method for increasing the solubility of roxithromycin, by providing an amorphous non-crystalline glass form (Form-II) of roxithromycin.

The method includes the steps of selecting roxithromycin from the group consisting of anhydrous roxithromycin or monohydrated roxithromycin; elevating the temperature of the roxithromycin to above the melting point thereof; and reducing the temperature of the melt sufficiently to allow it to set into an amorphous non-crystalline glass form (Form-II) of roxithromycin having relatively increased solubility.

Further Details of Respective Steps in the Method According to the Invention:

The first step of the method, according to a preferred embodiment of the invention is to select roxithromycin raw material from known commercially available anhydrous or monohydrate form.

The following step of the method is to melt the roxithromycin raw material at approximately 120 degrees Celsius and afterwards cool it to room temperature (25 degrees Celsius).

Alternatively, the roxithromycin raw material can be placed in a suitable container and heated to approximately 120 degrees Celsius in an oven. The melt is thereafter cooled to room temperature (25 degrees Celsius).

Further Analysis and Findings

It has surprisingly been found that Form-II is significantly more soluble compared to conventional anhydrous or monohydrate roxithromycin prepared according to prior art methods.

In further analysis of the novel Form-II, five test tubes with 100 mg of Form-II and 10 ml of one of the following solubility mediums respectively, namely, acetate buffer (pH 4.5), phosphate buffer (pH 6.8) and distilled water were filled.

The test tubes are then fixed to a rotating axis (54 rpm) and submerged in a water bath at 37 degrees Celsius±2 degrees Celsius for twenty-four hours. The contents of the test tubes are filtered through a 0.45 µm filter and subsequently the respective filtrates are diluted.

The concentrations of the five filtrates of Form-II and roxithromycin raw material respectively are determined by HPLC (high performance liquid chromatography) assay. The HPLC assay is performed utilising a mobile phase of 30 g/L ammonium dihydrogen phosphate buffer at pH 5.3. The pH is adjusted with sodium hydroxide solution and 310 ml of the buffer solution is mixed with 690 ml acetonitrile. A Luna C18 150 mm×4.6 mm column is used with a flow rate of 1.0 ml/min and a wavelength of 205 nm. Validation of this method provides a linear regression $r^2$ of 0.9998.

Figure 1:
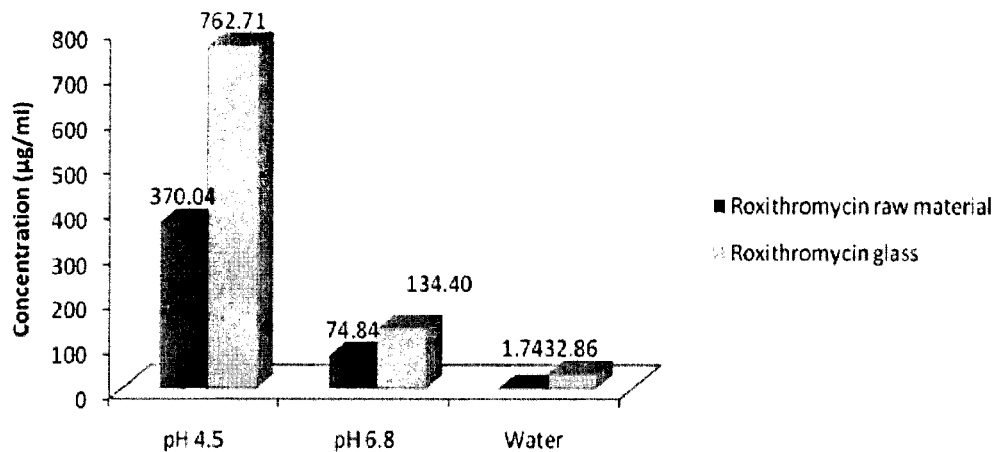
FIG. 1: is a solubility profile comparing the solubility of roxithromycin monohydrated raw material according to the prior art to amorphous non-crystalline glass form (Form-II) of roxithromycin according to a preferred embodiment of the present invention (Vertical axis: medium (pH); Horizontal axis: concentration (µg/ml))

Referring to FIG. 1, the solubility of roxithromycin raw material was determined as 370.0±8.3 µg/ml in acetate buffer (pH 4.5), 74.8±5.1 µg/ml in phosphate buffer (pH 6.8) and 1.7±0.6 µg/ml in distilled water. It was further determined that the solubility of Form-II as 762.71±2.6 µg/ml in acetate buffer (pH 4.5), 134.4±4.9 µg/ml in phosphate buffer (pH 6.8) and 32.86±3.5 µg/ml in distilled water. In fact, in comparison with the raw material, Form-II has a twofold (106%) improvement in solubility in pH 4.5 medium, a 1.8 fold (80%) improvement in pH 6.8 and an 18.8 fold (1789%) improvement in distilled water as medium. The HPLC analysis also showed that Form-II was chemically stable. It was found that the amorphous non-crystalline glass form (Form-II) of roxithromycin is at least 100%, more particularly at least 1500% more soluble than anhydrous roxithromycin or monohydrated roxithromycin in water. In fact, it was found that the amorphous non-crystalline glass form (Form-II) of roxithromycin was 1798% more soluble in water than monohydrated roxithromycin having a theoretical solubility of 1.8 µg/ml. It was further found that the amorphous non-crystalline glass form (Form-II) of roxithromycin is at least 30%, more particularly at least 75% more soluble than anhydrous roxithromycin or monohydrated roxithromycin between pH 4.5 to 6.8. In fact, it was found that the amorphous non-crystalline glass form (Form-II) of roxithromycin was 80% more soluble in pH 6.8 and 106% more soluble in pH 4.5 than monohydrated roxithromycin having a theoretical solubility of 370.0 µg/ml and 74.8 µg/ml.

Figure 2:
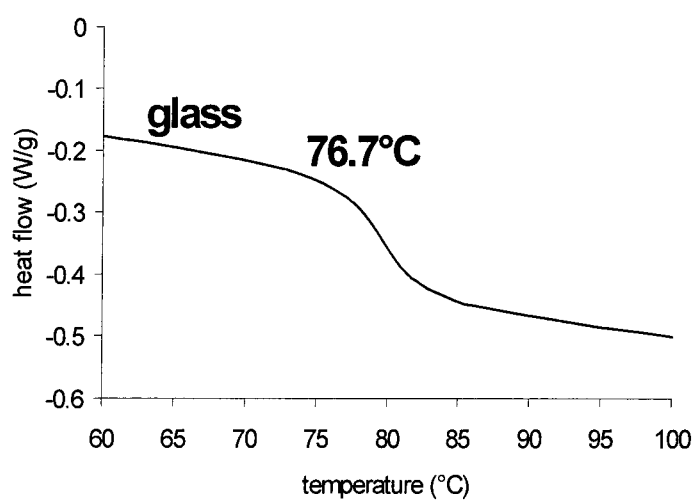
FIG. 2: is a DSC (differential scanning calorimetry) thermogram of Form-II (Vertical axis: heat flow (W/g); Horizontal axis: temperature (degrees Celsius))

Referring to FIG. 2, it was established that Form-II undergoes glass transition at 76.7 degrees Celsius where the composition changes from a hard, glass like state to a rubber like state. The transition further appears as a step transition in FIG. 2, confirming that Form-II is a glassy form of roxithromycin.

Figure 3:
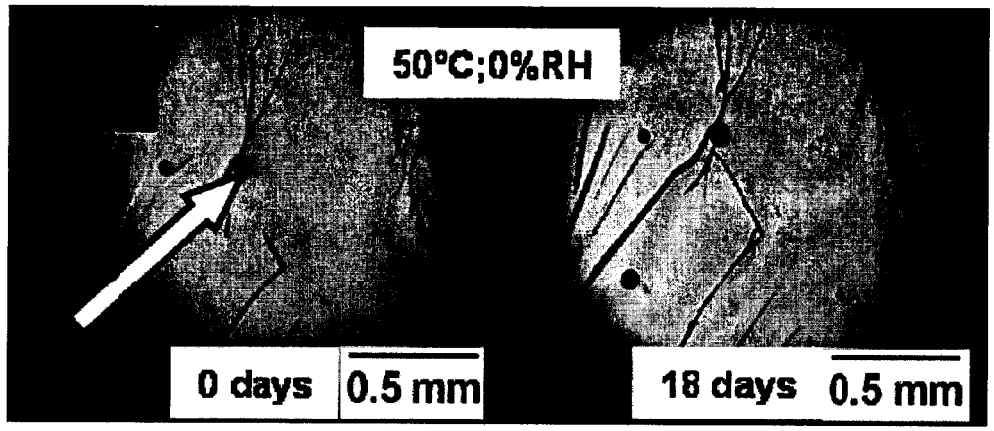
FIG. 3: is a microscopy image of Form-II exposed to 50 degrees Celsius at zero percent relative humidity.
Figure 4:
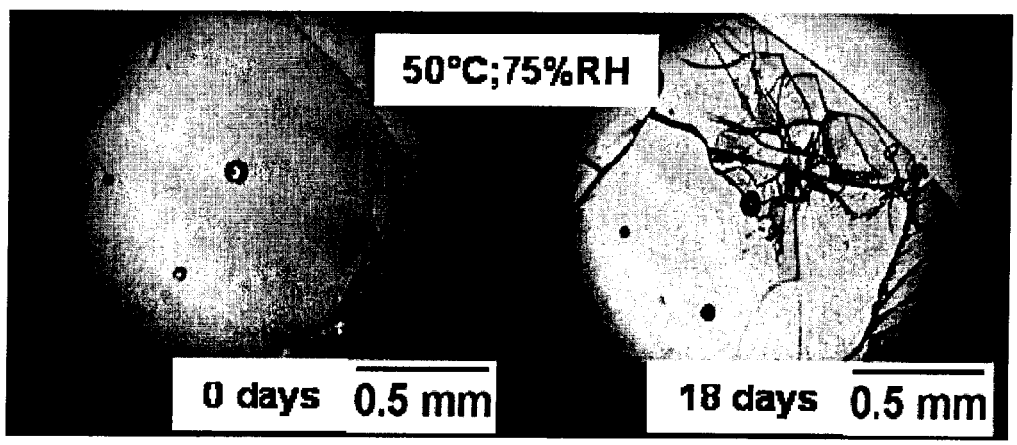
FIG. 4: is a microscopy image of Form-II exposed to 50 degrees Celsius at 75 percent relative humidity.

Form-II was further subjected to a temperature of 50 degrees Celsius at respectively zero (FIG. 3) and 75% relative humidity (FIG. 4) for 18 days. Form ll indicated no crystallisation after 18 days exposure to above conditions.

Figure 5:
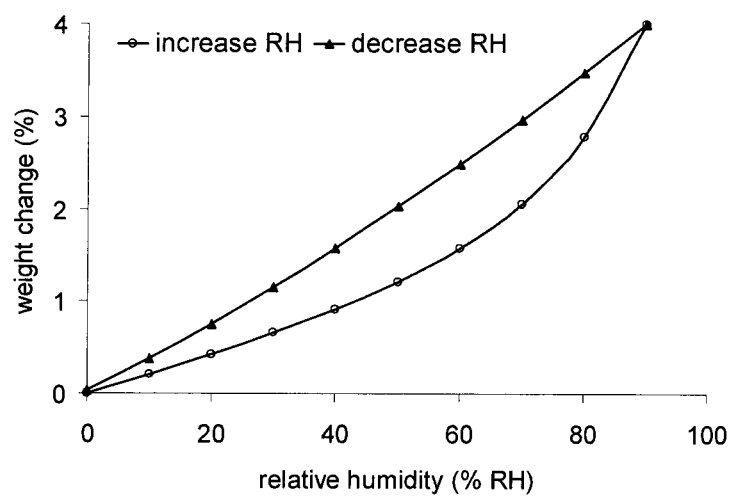
FIGS. 5 and 6: are the results of vapour sorption experiments for Form-II (FIG. 5) and prior art roxithromycin monohydrated raw material (FIG. 6) (Vertical axis: weight change (percentage); Horizontal axis: relative humidity (degrees Celsius RH))
Figure 6:
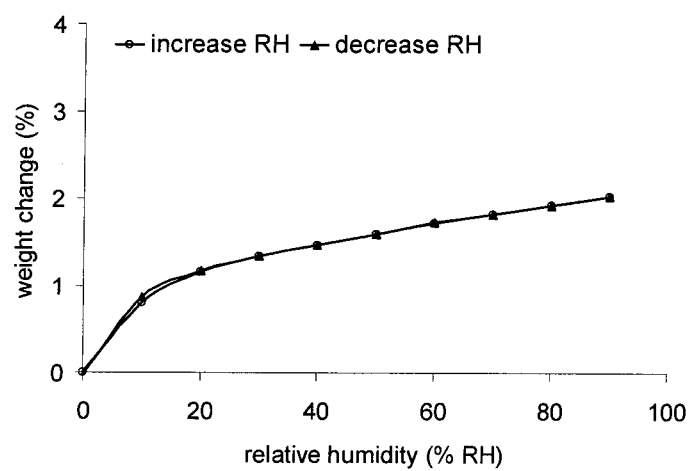

The results of the vapour sorption experiments of Form-II and the crystalline raw material are shown in FIGS. 5 and 6 respectively.

According to the moisture isotherm, Form-II showed an insignificant increase in weight (approximately 1.5%) at relative humidity up to 60% relative humidity (RH), and thereafter a sharp increase in weight (up to 4%) from 70 to 90% RH. The sharp increase is attributed to the condensation of water on the sample holder. Upon decreasing the humidity (from 90 to 0% RH) the sample showed a weight loss of 4% and returned to its starting weight.

It is therefore submitted that Form-II did not transform into a crystalline solid but remained amorphous, and high levels of moisture did not induce crystallization. Therefore it can be submitted that an increase in humidity do not change the solid-state properties of Form-II, as is evident in the sorption profile (FIGS. 5 and 6).

Figure 7:
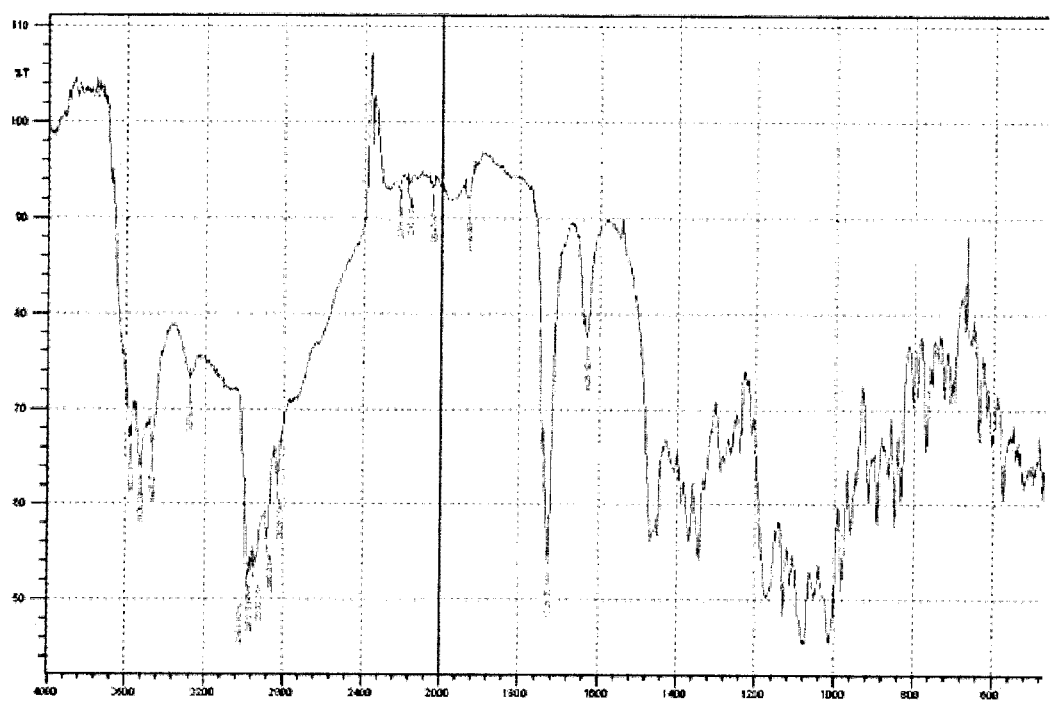
FIG. 7: is an infra-red (IR) spectrum obtained for prior art roxithromycin monohydrated raw material (Vertical axis: transmittance (percentage); Horizontal axis: wavelength $(cm^{-1})$)
Figure 8:
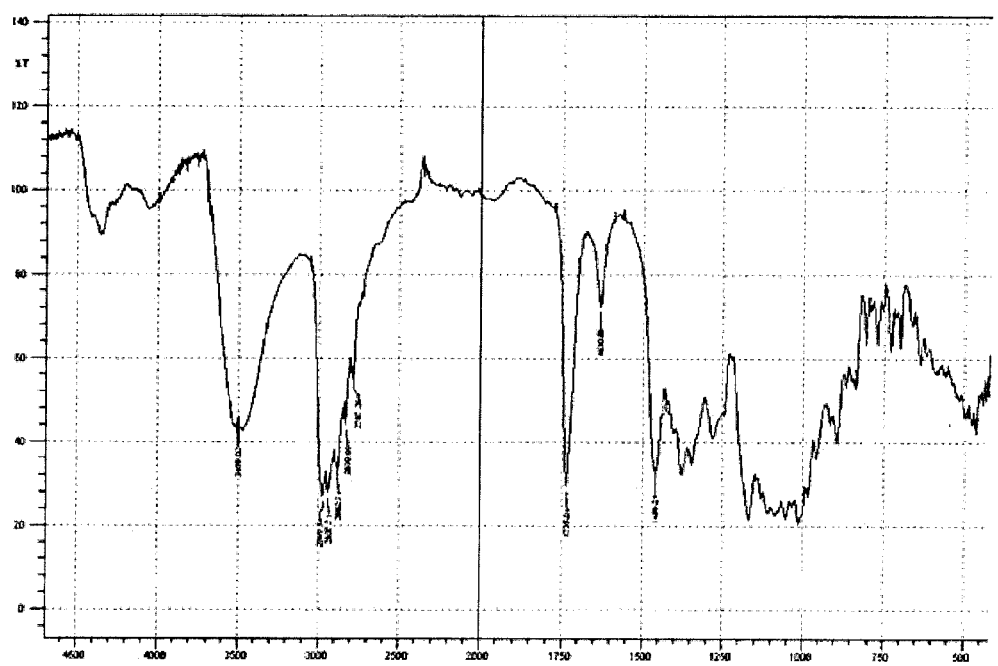
FIG. 8: is an IR spectrum of amorphous non-crystalline glass form (Form-II) of roxithromycin according to the invention (Vertical axis: transmittance (percentage); Horizontal axis: wavelength $(cm^{-1})$)

Referring to FIGS. 7 and 8, the infra-red (IR) spectrum wavelengths for both the raw material (FIG. 7) and the amorphous non-crystalline glass form (Form-II) of roxithromycin (FIG. 8) can be summarised as follow:

| Raw material | Amorphous non-crystalline glass form (Form-II) of roxithromycin |
| --- | --- |
| 3577.15 | No peak |
| 3526.03 | No peak |
| No peak | 3490.34 |
| 3465.27 | No peak |
| 3276.24 | No peak |
| 2206.66 | No peak |
| 2171.94 | No peak |
| 2043.67 | No peak |
| 1930.83 | No peak |

The most distinguishing difference between the IR spectrum of the raw material (FIG. 7) in comparison with the IR spectrum obtained from the amorphous non-crystalline glass form (Form-II) of roxithromycin (FIG. 8) lies between wavenumbers 3580 to 3464 $cm^{-1}$.

The IR-spectrum of the raw material (FIG. 7) displays three separate, clearly distinguishable peaks at 3577.15, 3526.03 and 3465.27 $cm^{-1}$. This is in contrast to the amorphous non-crystalline glass form (Form-II) of roxithromycin which only shows one broad peak at: 3490.34 $cm^{-1}$.

Figure 9:
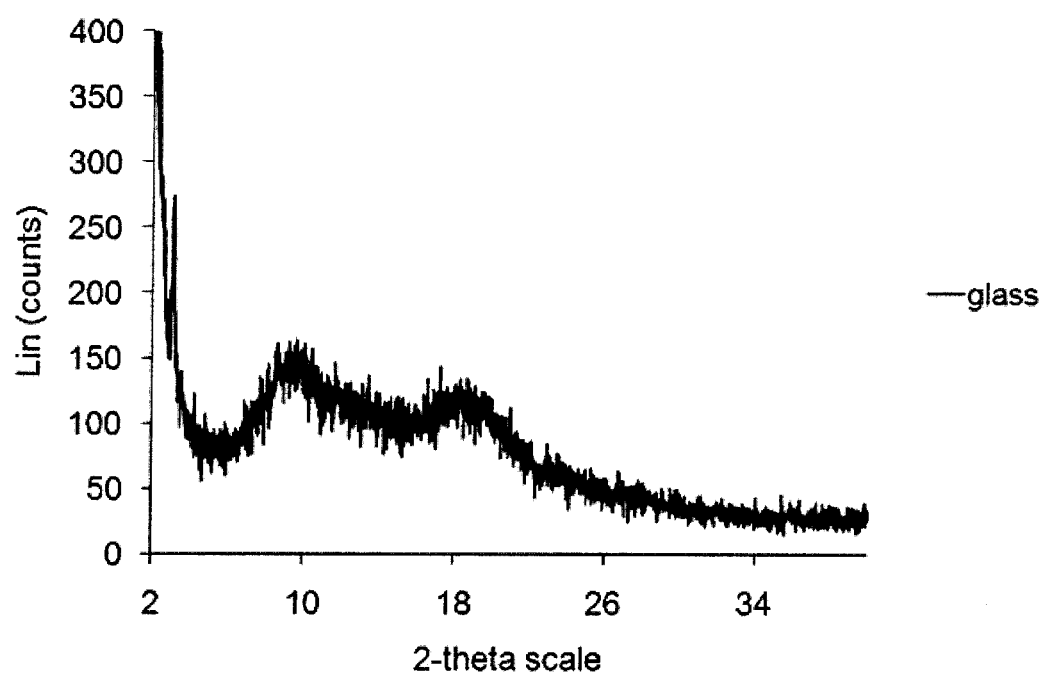
FIG. 9: is a characteristic XRPD (x-ray powder diffraction pattern) of amorphous non-crystalline glass form (Form-II) of roxithromycin (Vertical axis: intensity (Lin (counts)); Horizontal axis: 2 Theta (degrees)).

Referring to FIG. 9, the amorphous non-crystalline glass form (Form-II) of roxithromycin XRPD pattern exhibits the characteristic amorphous halo generally obtained with amorphous forms.

It will be appreciated that the disadvantages associated with prior art forms of roxithromycin, namely anhydrous and monohydrate forms, could be alleviated with the method according to the invention. In particular, the absorption and bioavailability of roxithromycin could be increased as a result of the increased water-solubility of Form-II. Moreover, reduced quantities of Form-II would be required in use in treating patients suffering from opportunistic illnesses associated with immune deficiency conditions, resulting not only in reduced risk to side-effects but to a reduced cost in treatment.

Applicant thus foresees that Form-II would not only present a relatively cheaper alternative to conventional production and manufacturing methods, but would also present a product that is superior in solubility to conventional anhydrous or monohydrate forms of roxithromycin.

Amorphous non-crystalline glass form (Form-II) of roxithromycin is formulated for administration in any convenient way and the invention includes within its scope pharmaceutical compositions comprising amorphous non-crystalline glass form (Form-II) of roxithromycin adapted for use in human or veterinary medicine.

The pharmaceutical compositions are presented for use in a conventional manner with the aid of a pharmaceutically acceptable carrier or excipient and may also contain, if required, other active ingredients. The amorphous non-crystalline glass form (Form-II) of roxithromycin is typically formulated for oral, buccal, topical or parenteral administration.

Oral administration is the preferred dosage form, particularly in the form of tablets and capsules. The pharmaceutical composition for oral administration conveniently takes the form of enteric coated tablets, capsules, powders, solutions, syrups or suspensions prepared by conventional means with acceptable excipients. Buccal administration compositions take the form of tablets or lozenges formulated in conventional manner.

The amorphous non-crystalline glass form (Form-II) of roxithromycin is further formulated for parenteral administration by bolus injection or continuous infusion. Formulations for injection are presented in unit dosage forms in ampoules, or in multi-dose containers, with an added preservative. The compositions further take such forms as suspensions, solutions or emulsions in oily or aqueous vehicles, and contain formulatory agents such as suspending, stabilising and/or dispersing agents.

Alternatively, the active ingredient is in powder form for reconstitution with a suitable vehicle.

The amorphous non-crystalline glass form (Form-II) of roxithromycin is yet further formulated in topical applications, comprising ointments, creams, gels, lotions, powders, transdermal patches, dermal patches or sprays prepared in a conventional manner.

The amorphous non-crystalline glass form (Form-II) of roxithromycin is yet further formulated in rectal and vaginal compositions such as suppositories or retention enemas containing conventional suppository bases such as cocoa butter or other glycerides as well as douches and pessary.

For oral administration a convenient daily dosage regime of amorphous non-crystalline glass form (Form-II) of roxithromycin is currently 1 to 2 doses to the total of 150 mg to 300 mg per day, dependent upon the age and condition of the patient.

It will be appreciated further that variations in detail are possible with a method for preparing a medicament and a medicament prepared with such a method, according to the invention without departing from the scope of this disclosure.

The invention claimed is:
1. A method of increasing the solubility of roxithromycin comprising:
  providing roxithromycin selected from the group consisting of anhydrous roxithromycin or monohydrated roxithromycin;
  elevating the temperature of the roxithromycin to between 100 and 140° C.; and
  reducing the temperature of the roxithromycin sufficiently to allow it to set into an amorphous non-crystalline glass form of roxithromycin having relatively increased solubility without decreasing the stability thereof.

2. An amorphous non-crystalline glass form of roxithromycin prepared according to the method of claim 1.

3. The amorphous non-crystalline glass form of roxithromycin according to claim 2 having an infra-red spectrum having at least one characteristic peak at approximately 3580 to 3464 cm$^{-1}$.

4. The amorphous non-crystalline glass form of roxithromycin according to claim 2 having an infra-red spectrum, substantially as depicted in FIG. 8.

5. The amorphous non-crystalline glass form of roxithromycin according to claim 2 exhibiting a powder X-ray diffraction pattern substantially as depicted in FIG. 9.

6. The amorphous non-crystalline glass form of roxithromycin according to claim 2 displaying a differential scanning calorimetry thermogram substantially as depicted in FIG. 2 and exhibiting a glass transition between 75 and 78° C.

7. The amorphous non-crystalline glass form of roxithromycin according to claim 2 having at least 100% increased solubility over anhydrous roxithromycin or monohydrated roxithromycin in water.

8. The amorphous non-crystalline glass form of roxithromycin according to claim 7 having at least 1500% increased solubility over anhydrous roxithromycin or monohydrated roxithromycin in water.

9. The amorphous non-crystalline glass form of roxithromycin according to claim 2 having at least 30% increased solubility over anhydrous roxithromycin or monohydrated roxithromycin in water between pH 4.5 to 6.8.

10. The amorphous non-crystalline glass form of roxithromycin according to claim 9 having at least 75% increased solubility over anhydrous roxithromycin or monohydrated roxithromycin in water between pH 4.5 and 6.8.

11. A pharmaceutical composition comprising a pharmaceutically effective amount of an amorphous non-crystalline glass form of roxithromycin prepared in accordance with the method of claim 1 and at least one pharmaceutically acceptable carrier or diluent.

12. A method of treating a patient suffering from opportunistic diseases associated with immune deficiency conditions including the step of administering to such a patient a pharmaceutically effective amount of an amorphous non-crystalline glass form of roxithromycin prepared in accordance with the method of claim 1.

* * * * *